(12) United States Patent
Kurukchi et al.

(10) Patent No.: US 9,969,944 B2
(45) Date of Patent: May 15, 2018

(54) DISSOLVED OIL REMOVAL FROM QUENCH WATER OF GAS CRACKER ETHYLENE PLANTS

(71) Applicant: Janus Technology Solutions, LLC, Houston, TX (US)

(72) Inventors: Sabah A. Kurukchi, Houston, TX (US); Joseph M. Gondolfe, Magnolia, TX (US)

(73) Assignee: Janus Technology Solutions, LLC, Spring, TX (US)

( * ) Notice: Subject to any disclaimer, the term of this patent is extended or adjusted under 35 U.S.C. 154(b) by 0 days. days.

(21) Appl. No.: 15/714,546

(22) Filed: Sep. 25, 2017

(65) Prior Publication Data
US 2018/0086987 A1 Mar. 29, 2018

Related U.S. Application Data

(60) Provisional application No. 62/398,904, filed on Sep. 23, 2016.

(51) Int. Cl.
*C02F 1/00* (2006.01)
*C02F 1/04* (2006.01)
(Continued)

(52) U.S. Cl.
CPC .............. *C10G 33/04* (2013.01); *B01D 1/00* (2013.01); *B01D 3/38* (2013.01); *B01D 11/0488* (2013.01);
(Continued)

(58) Field of Classification Search
CPC .. C02F 1/001; C02F 1/004; C02F 1/02; C02F 1/04; C02F 1/048; C02F 1/20; C02F 1/26; C02F 9/00; C02F 1/043; B01D 1/00; B01D 3/00; B01D 3/38; B01D 11/04; B01D 11/0426; B01D 11/0488; B01D 11/0492; B01D 17/02; B01D 17/0208; B01D 17/0214; B01D 21/00; B01D 21/0039;
(Continued)

(56) References Cited

U.S. PATENT DOCUMENTS 3,492,222 A   1/1970 Van Tassell
3,507,782 A * 4/1970 Kurland ................. B01D 12/00
                                             208/188
(Continued)

OTHER PUBLICATIONS

"Quench Water Clean-Up" by Koenig & Banerjee. Published on Mar. 31, 1992 at the AIChE Spring meeting.
(Continued)

*Primary Examiner* — Joseph Drodge
(74) *Attorney, Agent, or Firm* — Tumey L.L.P.

(57) ABSTRACT

A method for removing dissolved hydrocarbons from water may comprise: cracking a mixed hydrocarbon stream in a cracking furnace to produce a cracked gas effluent; quenching the cracked gas effluent in a quench water tower with quench water to produce a quenched gas stream and a spent quench water stream comprising water, tars, heavy aromatic hydrocarbons, gasoline, dissolved oil, and dispersed oil; feeding the spent quench water stream to a liquid-liquid extraction unit wherein the liquid-liquid extraction unit removes at least a portion of the dissolved oil and produce an extracted effluent stream.

20 Claims, 3 Drawing Sheets

(51) Int. Cl.
*C02F 1/26* (2006.01)
*C02F 9/00* (2006.01)
*B01D 1/00* (2006.01)
*B01D 3/00* (2006.01)
*B01D 11/04* (2006.01)
*C07C 4/16* (2006.01)
*C07C 5/42* (2006.01)
*C10G 33/04* (2006.01)
*B01D 3/38* (2006.01)

(52) U.S. Cl.
CPC .......... *B01D 11/0492* (2013.01); *C02F 1/001* (2013.01); *C02F 1/048* (2013.01); *C02F 9/00* (2013.01); *C07C 4/16* (2013.01); *C07C 5/42* (2013.01); *C10G 2400/20* (2013.01); *C10G 2400/22* (2013.01)

(58) Field of Classification Search
CPC ........ B01D 36/00; B01D 36/04; B01D 37/00; C10G 33/04; C10G 33/06; C10G 9/00; C10G 9/002; C10G 2300/807; C10G 2400/20; C10G 2400/22; C07C 4/16; C07C 5/42; C07C 7/00; C07C 7/005; C07C 7/10
USPC ....... 210/634, 638, 774, 799, 804, 806, 177, 210/182, 259, 511, 513; 196/14.52, 46, 196/46.1, 104, 105; 208/67, 95, 96, 208/100–106, 130, 187; 585/802, 818, 585/833
See application file for complete search history.

(56) References Cited

U.S. PATENT DOCUMENTS

| | | | |
|---|---|---|---|
| 3,515,766 A * | 6/1970 | Root | C07C 5/321 210/663 |
| 3,868,094 A | 2/1975 | Hovis | |
| 3,878,094 A | 4/1975 | Conley et al. | |
| 4,009,218 A | 2/1977 | Uitti | |
| 4,014,786 A * | 3/1977 | Potter | B01D 12/00 48/211 |
| 4,336,129 A | 6/1982 | Yoshimura et al. | |
| 4,402,711 A * | 9/1983 | Stellaccio | C10J 3/00 210/774 |
| 4,800,025 A | 1/1989 | Bibaeff | |
| 4,802,978 A | 2/1989 | Schmit et al. | |
| 5,080,802 A | 1/1992 | Cairo et al. | |
| 5,656,173 A | 8/1997 | Jordan et al. | |
| 6,120,650 A * | 9/2000 | Nye | B01D 5/0036 196/110 |
| 6,395,952 B1 * | 5/2002 | Barchas | C10G 70/02 585/809 |
| 6,576,132 B2 * | 6/2003 | Kurukchi | B01D 3/38 210/634 |
| 2009/0036727 A1 * | 2/2009 | Kurukchi | B01D 53/1406 585/854 |
| 2014/0251874 A1 * | 9/2014 | Barroeta | C10G 31/08 208/298 |
| 2015/0240366 A1 * | 8/2015 | Arnst | C23F 15/00 422/7 |

OTHER PUBLICATIONS

Mullenix, Moyer & Wittman, "DOX Unit Operating Experience in Vista's Ethane Cracker" Paper No. 17C, 1993 AIChE Spring Meeting Mar. 31, 1993, 21 pages.

Guyot, Balouet, Wines and Bretelle "Increase Ethylene Processing Capacity and Efficiency with Improved Liquid/Liquid Separation," 16 pages, Undated.

Cockshutt and Dennehy, "Methods for Successful Process Selection for Quench Water Cleanup" Paper No. 17D. Prepared for Presentation AIChE spring Meeting—Houston, TX. 15 pages, Undated.

* cited by examiner

DISSOLVED OIL REMOVAL FROM QUENCH WATER OF GAS CRACKER ETHYLENE PLANTS

BACKGROUND

Dissolved Oil Removal (DOR) Unit is an additional liquid-liquid extraction process, using aromatic rich hydrocarbon solvent, that may remove reactive dissolved hydrocarbons from pretreated net quench water used in the process of dilution steam generation of steam cracker plants. The step of pretreating may remove dispersed oil from the aqueous phase of the net quench water.

Present technologies for pretreating net quench water may be described as free dispersed oil coalescing units. Some units may include filters followed by a coalescer, Dispersed Oil Extractor (DOX) system, and Induced Gas Floatation (IGF) system. All these units may coalesce dispersed oil droplets in the net quench water and remove the coalesced oil from the net quench water. None of the aforementioned units are capable of removing the dissolved oils that are in the bulk aqueous phase. Some of the hydrocarbons present in the bulk aqueous phase may react in units downstream of the coalescing unit which may cause fouling of dilution a steam generator and a gaseous hydrocarbon steam saturator. A DOR unit may be used to further treat pretreated net quench water to reduce the amount of dissolved hydrocarbons in the net quench water. Reduction or removal of dissolved hydrocarbons may reduce fouling of the dilution steam generator and the gaseous hydrocarbon steam saturator.

Base petrochemicals such as olefins (alkenes) may be produced in steam cracking plants from saturated aliphatic hydrocarbon feedstocks, such as ethane, propane, butanes or higher molecular weight hydrocarbon mixtures such as naphtha, atmospheric and/or vacuum gas oils, and the like. Generally, pressures may be close to atmospheric (e.g., from about 1.5 to 2.5 barg.), and temperatures may be from approximately 700° C. to approximately 870° C. Steam may be added to the hydrocarbon feed to reduce the hydrocarbon partial pressure. Steam-to-hydrocarbon feed ratios may be generally 0.3-0.4:1 on a weight basis for light hydrocarbon feedstocks such as ethane or propane, and butanes, respectively. The saturated hydrocarbon-steam mixture may be thermally cracked to lower molecular weight unsaturated hydrocarbons. Cracking product reactions may include ethylene predominately, followed by propylene, and then various quantities of $C_4$, $C_5$ and $C_6$ mono- and diolefinic hydrocarbons, with a lesser quantity of $C_7$ and higher weight saturated and unsaturated aliphatic, cyclic and aromatic hydrocarbons.

Additionally, the thermal cracking process may produce some molecules that tend to combine to form high molecular weight materials which can be categorized within the boiling range of "fuel oil" and heavier compounds categorized as "tar". Tar is a high-boiling point, viscous, reactive material that can foul equipment under certain conditions. In general, feedstocks containing higher boiling materials tend to produce greater quantities of tar. Unsaturated hydrocarbons are reactive and may polymerize upon exposure to high temperatures which may cause fouling of equipment.

One reason a steam cracking unit may be using ethane as a feedstock is because ethane is a co-product of natural gas from shale gas production, and has limited value for uses other than as a feedstock to a steam cracker unit. As natural gas demand and production rates grow for supplying electrical power and home heating needs, ethane availability may increase beyond its domestic regional demand. Since ethane cannot be readily or economically transported, regional demand is important and where its availability exceeds regional demand, its price is reduced. In many regions, ethane feed costs may be 25% to 50% of other steam cracker feedstocks such as propane, butanes or naphthas. This economic scenario gives rise to a large advantage to producing ethylene using low cost ethane feedstock. In addition, energy costs and capital investments for a steam cracker using ethane feedstock may be far below the costs for using propane, butanes or naphthas as feedstock(s).

Following thermal cracking of saturated hydrocarbons, the effluent from the pyrolysis reactor must be rapidly cooled to a temperature at which no additional reaction occurs. This rapid cooling may be effected by indirectly cooling the effluent in typical Transfer Line Exchanger(s) (TLE) which generates high pressure steam and then further directly cooled by circulating water created from condensation of steam within a Quench Water Tower.

For gaseous feedstocks (ethane, propane and butanes), a Quench Oil Tower (QOT) may not be required because only small amounts of $C5^+$ liquids may be produced. For these feedstock types, a simple Quench Water Tower (QWT) is used to cool the effluent gas from the TLE.

The cracked gas may be further cooled in the QWT by direct contact with quench water. Typically, the bottoms stream leaving the quench tower feeds an oil-water separator (OW/S) drum, which function as a three-phase separator, with a light hydrocarbon phase that floats on water, and the tar which sinks in water, as the bottom phase, and water as the middle phase. Even in the case of cracking an ethane feed which may have a relatively lower tar yield than other feedstocks, the small amounts of tar may build up and over time and foul downstream units. In particular, water leaving the OW/S may contain enough heavy oils and tar, which has a specific gravity close to that of water, to potentially cause downstream fouling of the quench circuit. This can also potentially result in the fouling of downstream heat exchangers and water stripping towers, which, when fouled, must be taken offline for cleaning.

The gross Quench Water (QW), from the OW/S, may contain residual fine solid particles, unsettled free oil, emulsified oil, and dissolved hydrocarbons. The majority of this gross QW may be recirculated for low-level heat recovery within the ethylene plant before returning to the QWT. The net raw QW may be either: (1) used to generate dilution steam for steam cracking as a close-loop system, or (2) purged to battery limits as an open-loop system. The net QW may be processed to remove the residual suspended solids, as well as free and emulsified oil, in order to prevent or reduce fouling in a downstream dilution steam generation system. Alternatively, if the excess raw water were simply purged to battery limits, it would still be necessary to remove organic impurities (e.g. benzene, dienes, and other carcinogens) to such an extent that it could be discharged into local streams without causing pollution.

At present, the net QW is treated by coalescing its free and dispersed oil using any combination of the available coalescing technologies including: filter-coalescer, Natco DOX (Dispersed Oil Extraction) unit, and IGF (Induced Gas Floatation). These technologies are effective in removing most of the free and dispersed oil but remain incapable of removing the dissolved unsaturated hydrocarbons. Any remaining dissolved unsaturated hydrocarbons in the QW may polymerize leading to fouling of the steam generation equipment. Additionally, discharges of net QW and blowdowns from dilution steam generators and gaseous hydrocarbon saturators may have difficulties in meeting the environmentally required oil and benzene content.

BRIEF DESCRIPTION OF THE DRAWINGS

These drawings illustrate certain aspects of some examples of the present disclosure, and should not be used to limit or define the disclosure.

DETAILED DESCRIPTION

Figure 1:
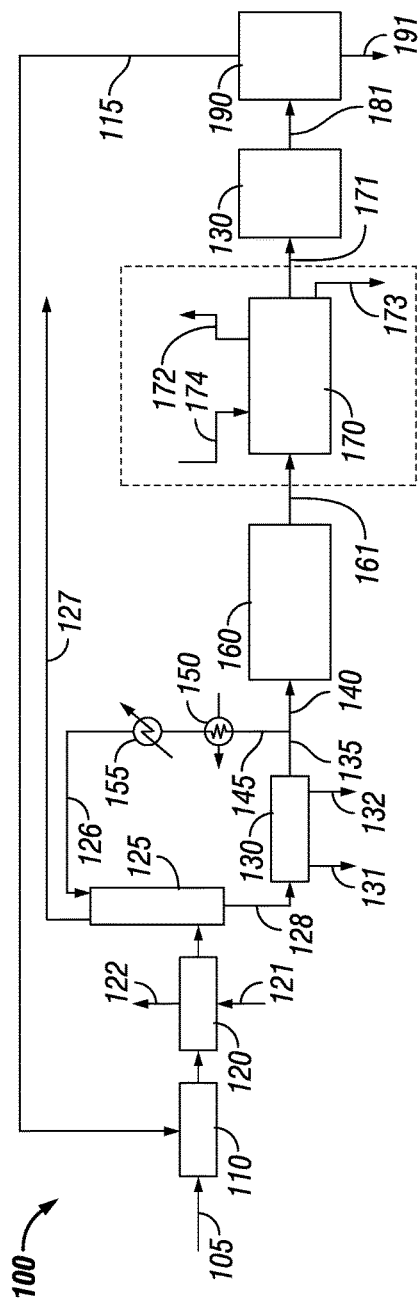
FIG. 1 is a schematic illustration of a gas cracking plant comprising a dissolved oil removal unit.

The present disclosure is directed to removal of polymerizable compounds from a quench water stream in a gas cracking plant and in one or more embodiments to a liquid-liquid extractor to remove the polymerizable compounds. Commercially available technologies in ethylene plants for treating the net quench water (QW) may involve the removal of suspended solids and coalescing dispersed oil without affecting the dissolved hydrocarbon content. QW may comprise tars, heavy aromatic hydrocarbons with a specific gravity of greater than 1, gasoline, dissolved oil, dispersed oil, and other hydrocarbon species. The gross QW, from the OW/S, may comprise residual fine suspended solids in the range of 20 to 30 ppmw, unsettled oil and grease of 900-1200 ppmw, and total organic carbon that include both dispersed and dissolved HC's in the range from 1500-2000 ppmw carbon. These ranges are merely illustrative and one of ordinary skill would understand that the process disclosed herein may be applied to ranges that are smaller or larger than those instantly disclosed. Commercially available technologies may involve addition of gasoline or other commercial proprietary emulsion breaking chemicals to enhance phase separation, and filters and/or hydro-cyclone followed by coalescer.

Filter-coalescer units are prevalent in several olefin plants built prior the 1990's. At the time of the plant constructions, there were no benzene regulations that had to be met for the water blowdown stream. The filter-coalescer units may include a filter and a coalescer. The filter may capture coke fines as particulate matter. Typically, there may be two sets of filters, a coarse type (e.g., 100-300 microns size) and a fine type (e.g., 10-30 microns). These filters may be made of any suitable material, including, but not limited to, fabric or fibers, and generally may be a cartridge type. Some plants may use metallic filters that may be back flushed with QW. This technique may reduce the risk of benzene exposure to the operators.

The water from the filter may be transferred to the coalescer, which may be a horizontal drum or oil-water separator designed to segregate oil and water. The design of the drum may be based on the fundamental principles of Stoke's Law. The separated oil floats to the top and oil free water is withdrawn from the bottom. Any tar or tar-like compounds collect in the bottom of the oil-water separator and may be removed intermittently. The coalescer efficiency of oil-water separation depends, for example, on the density difference of oil and water and how much residence time is available. Therefore, coalescers may be relatively large to be effective for this application.

A Dispersed Oil Extractor (DOX) system may be used to remove emulsified oil and suspended solids from the QW. The system may comprise a primary granular media coalescer filled with a multi-layer of different size granular material, followed by a vertical coalescer filled with carbon media that may further coalesce suspended oil. The oil coalescence may be finished in a horizontal separator containing a matrix plate section and a separation section that allows the separation of the three phases (light oil, treated QW and heavy oil). This system does not remove dissolved hydrocarbons from the treated QW.

Another system may include an Induced Gas Floatation (IGF) system. The IGF may remove emulsified oil and suspended solids from QW. Fine gas bubbles may be distributed uniformly through the fluid volume, providing efficient transport of oil and solids to the liquid surface for removal. When the oil contacts a gas bubble, it wets the surface of the bubble. The oil wetted bubbles may agglomerate due to attraction caused by surface tension forces and electrically charged particles. These bubbles then float to the top of the chamber and are skimmed off Suspended solids adhere to the bubbles and are skimmed off as well. Froth is removed via a simple skim trough that simplifies both the operation and maintenance. Skimming volume and frequency are automatically controlled.

The water leaving this IGF unit may be passed through a filter to polish the water and remove the remaining emulsified oil in the water. Pecan/Walnut shell media may resist oil fouling better than other media. The media may be cleaned using any suitable technique, including, but not limited to, back flushing with aromatic oil a few times a year. Only about 5-10% replenishing may be required per year of operation. The regeneration cycle may comprise a) fluidization; b) discharge to the flare or to the Quench Water Tower, c) settling and normalization. The froth collected from the IGF unit may be allowed to settle in a tank before the oil is sold as a product. The sludge from the bottom of the tank may be removed periodically and disposed with the heavy oil and tars. An additive may be added prior to the IGF unit to assist in oil & grease separation. Additionally, natural gas, fuel gas, or nitrogen may be used for flotation. The natural gas or fuel gas may then be burned in the furnaces. In examples with chemical injection prior to the IGF unit and a filter after the IGF unit, the recovery of hydrocarbons may be about 98% or greater. IGF treated water typically has less than amount 20 ppmw (parts per million by weight) free hydrocarbons.

In some examples, it may be necessary to clean the net QW to remove contamination before the net QW is used for generating dilution steam. Removing contamination may reduce or prevent fouling in downstream equipment such as a Low Pressure Water Stripper (LPWS), a Dilution Steam Generator (DSG), or a Gaseous Hydrocarbon Steam Saturator (GHSS). Furthermore, removal of contaminants may allow operation of the LPWS at temperature higher than 125° C., which may reduce the benzene content to below the environmental required benzene specification limits of <50 ppbw (parts per billion by weight) for blowdown discharge to the environment.

The previously mentioned technologies for treating net QW are found to be inadequate to meet the above two cleanup requirement since they can only address removal of solids and both the free and dispersed oil. Even if these coalescing technologies were to operate perfectly, they will leave behind in the partially treated net QW all the dissolved hydrocarbon in the net QW for dilution steam-make.

In some examples, the performance of a DOX unit in treating net QW from the oil-water separator unit may remove total organic carbon (TOC) to about 21% of the input TOC. Such equipment is available from the Schlumberger Company marketed as NATCO DOX. The dissolved hydrocarbons may largely consist of highly soluble unsaturated components of the oils in the QW, These unsaturated compounds may be highly reactive polymer precursors represented by styrene and indene as indicative dissolved oil species in the aqueous phase.

Styrene polymerization may produce a black or brown hard deposit while polyindene polymers may be yellowish. Because of frequent fouling of the DSG in the past, many DSG trays are removed during revamps and in new grass-root design to avoid fouling and limiting the DSG capacity. The removal of trays in the DSG means that any polymer formed may not be deposited in the DSG, but rather they may be carried with the dilution steam to the furnace where they will encounter much higher temperature and may cause more damaging fouling of the cracking furnace steel tubes.

As a result of the new requirements for low benzene content of <50 ppbw in the blowdown QW discharge and the disadvantages of the prior art processes in removing the dissolved polymer precursors from the net QW, an additional process step may be used for the removal of the dissolved hydrocarbons from the net QW. The combination of the previously described process steps used to remove the free and dispersed oil from the net QW using filter coalescer, DOX, IGF, or a combination thereof together with an additional step of extraction of the dissolved hydrocarbons may remove essentially all hydrocarbons present in the net QW before reaching the DSG or the GHSS. The process will meet the new benzene levels in the QW blowdown requirements and overcome the deficiencies of the prior art that resulted in fouling of the DSG and GHSS.

FIG. 1 illustrates a more detailed description of the disclosed techniques, in accordance with example embodiments. Process 100 illustrates a gas cracking process comprising a liquid-liquid extractor and a dilution steam generator. Gaseous hydrocarbon feedstock 105 may comprise ethane or propane and other trace hydrocarbons as defined within the Gas Processors Suppliers Association (GPSA) handbook. Gaseous hydrocarbon feedstock 105 may be delivered to the convection section in the upper part of the cracking furnaces 110. Gaseous hydrocarbon feedstock 105 may be first preheated in hydrocarbon preheat banks, not illustrated, prior to mixing with dilution steam 115. The hydrocarbon and dilution steam mixture may then be further preheated sequentially in the hydrocarbon dilution steam bank before leaving the convection section to cross over to the radiant coil inlets.

The heat required for the cracking reaction may be supplied by a radiant section in the lower part of the steam cracking furnace 110. In some embodiments, the radiant section may comprise floor fired burners. The burners firing rate may be controlled based on the average coil outlet temperature. Furnace effluent may be rapidly cooled in quench exchangers 120. Quench exchangers 120 may comprise any suitable heat exchangers such as, for example, double pipe exchangers or horizontal shell and tube transfer line exchanger (TLE) quench exchangers. Boiler feed water 121 may be supplied to quench exchanger 120 to generate steam 122 for use in other processes.

The heat exchanger effluent comprising cracked gasses may then be fed to a quench water tower 125 wherein the heat exchanger effluent may be further cooled by direct countercurrent contact with quench water 126. The cooled gas from the quench water tower overheads 127 may be transported to a cracked gas compressor.

A water and hydrocarbon mixture 128, may be collected in the bottom of the quench water tower, which may then be transported to oil-water separator 130. Oil-water separator 130 may separate a heavy phase, comprising tar and coke particles, from the bulk stream. A water-hydrocarbon interface may be established which may allow for separation of the remaining two phases. In the case of cracking an ethane feed, light tars may be produced which may have a specific gravity close to that of water. The tar yield may be high enough to cause the water leaving oil-water separator 130 to cause downstream fouling of the quench circuit. Accumulated tar and coke particles 131 may settle out from the quench water in oil-water separator 130 which may be stored in barrels or sent to an incinerator for disposal. A pyrolysis gasoline stream 132 may also be removed from oil-water separator 130 which may be delivered to a slop oil tank. Pyrolysis gasoline is a naphtha boiling range product with a high aromatics content that may be produced as a side product of the thermal cracking reaction. Oil-water separator 130 may operate in a temperature range of about 80° C. to about 90° C. and a pressure within about 90-100% of adiabatic saturation.

The hot raw quench water 135 from the oil-water separator 130 may be pumped and split into recirculating hot quench water 145 and a small net quench water NQW 140. The hot quench water 145 may be circulated through the quench water users 150 and then be further cooled in cooling water exchanger 155 to produce quench water 126. Quench water 126 may be returned to quench water tower 125.

The NQW 140 may be fed to an oil coalescing unit 160 which may separate out the solids, and both the free and dispersed oil and hydrocarbons from NQW 140. Oil coalescing unit 160 may comprise one or more coalescing units including filter-coalescer unit, Natco DOX (Dispersed Oil Extraction) Unit, induced gas floatation unit (IGF), or combination thereof as previously described.

The coalesced NQW 161 from the oil coalescing unit 160 may be treated for removal of dissolved hydrocarbon in dissolved oil removal unit 170. Dissolved Oil Removal (DOR) unit 170 may comprise a liquid-liquid extractor and a solvent regenerator. The coalesced NQW 161 may be contacted with aromatic rich solvent in dissolved oil removal unit 170 which may extract the unsaturated dissolved hydrocarbons from NQW 161. Treated NQW 171 may be pumped to low pressure water stripper, LPWS, 180. The contaminated solvent from dissolved oil removal unit 170 may be distilled in a solvent regenerator to separate out the light contaminants 172, which may be sent to a flare, and a heavy contaminants stream 173 comprising spent solvent and dissolved hydrocarbons. The regenerated solvent stream may be combined with a makeup solvent to generate a solvent stream 174 that is fed into the dissolved oil removal unit 170.

The low pressure water stripper 180 may heat treated NQW 171 to strip its dissolved hydrocarbons and acid gases such as $H_2S$ and $CO_2$. Clean water 181 from low pressure water stripper 180 may be essentially free of all volatile hydrocarbons, less than about 15 ppmw, at this pressure of about 10-15 psig. Clean water 181 may be pumped to the dilution steam generator (DSG) 190 where it may be boiled to generate dilution steam 115. Dilution stream 115 may be transported to the cracking furnaces 110 to mix with gaseous hydrocarbon feedstock 105. A small part of the water may be rejected as dilution steam blowdown 191.

Figure 2:
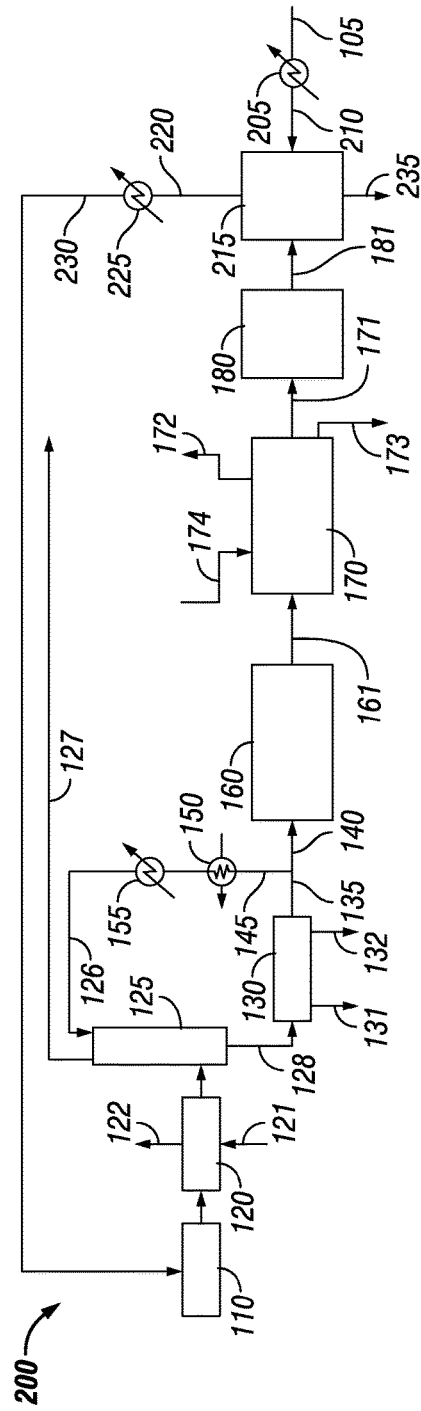
FIG. 2 is a schematic illustration of a gas cracking plant comprising a dissolved oil removal unit.

FIG. 2 illustrates a process 200 for gas cracking comprising a liquid-liquid extractor and a gaseous hydrocarbon saturator, in accordance with example embodiments. Gaseous hydrocarbon feedstock 105, may comprise ethane or propane. Gaseous hydrocarbon feedstock 140, may be heated in an exchanger 205. Heated hydrocarbon gas 210 may be fed to gaseous hydrocarbon saturator 215 where it may be mixed with clean water stream 181 to evaporate the water. Clean water stream 181 which may be essentially free of hydrocarbons from low pressure water stripper 180. Mixed hydrocarbon and steam stream 220 from gaseous hydrocarbon saturator 215 may be further heated in heat exchanger 225 to produce superheated stream 230. Superheated stream 230 may be transported to cracking furnace 105 to crack the gaseous hydrocarbons present in superheated stream 230. The cracked gas furnace effluent may be rapidly cooled in quench exchanger 120. Quench exchanger 120 may comprise double pipe exchangers, horizontal shell and tube transfer line heat exchangers, and combinations thereof. The heat may be exchanged against boiler feed water 121 to generate steam 122.

The process gas may be fed to quench water tower 125 wherein the process gases may be further cooled by direct countercurrent contact with quench water 126. The cooled gas from the quench water tower overheads 127 may be transported to the cracked gas compressor. A portion of the feed stream to quench water tower 125 may dissolve into water present in quench water tower 125. A water and hydrocarbon mixture 128 may collect in the bottom of quench water tower 125 and flow to oil-water separator 130. Oil-water separator 130 may be configured as previously described in FIG. 1. Accumulated tar and coke particles 131 may settle out from the quench water in oil-water separator 130. The particles may be stored in barrels or be sent to an incinerator for disposal. Pyrolysis gasoline 132 from oil-water separator 130 may be delivered to a slop oil tank.

Hot raw quench water 135 from oil-water separator 130 may be pumped and split into recirculating hot quench water 145 and a small net quench water NQW 140. The hot quench water 145 may be circulated through the quench water users 150 and cooled in cooling water exchanger 155 and then returned to the tower.

The NQW 140 may be fed to an oil coalescing unit 160 which may separate out any solids, and both the free and dispersed oil from NQW 140, and may include one or more coalescing unit including filter-coalescer unit, Natco DOX (Dispersed Oil Extraction) Unit, induced gas floatation unit IGF, or combinations thereof as previously described.

Coalesced NQW 161 from the oil coalescing unit 160 may be treated for removal of its dissolved hydrocarbon in dissolve oil removal (DOR) unit 170 which may comprise a liquid-liquid extractor and a solvent regenerator. Coalesced NQW 161 may be contacted with aromatic rich solvent in the liquid-liquid extractor which may extract the unsaturated dissolved hydrocarbons from coalesced NQW 161. Treated NQW 171 from DOR unit 170 may flow to the low pressure water stripper LPWS 180. The contaminated solvent from dissolved oil removal unit 170 may be distilled in a solvent regenerator to separate out the light contaminants 172, which may be sent to a flare, and a heavy contaminants stream 173 comprising spent solvent and dissolved hydrocarbons. The regenerated solvent stream may be combined with a makeup solvent to generate a solvent stream 174 that is fed into the dissolved oil removal unit 170.

Low pressure water stripper (LPWS) 180 may preheat the water and strip dissolved hydrocarbons and acid gases such as $H_2S$ and $CO_2$. Clean water 181 from low pressure water stripper 180, may be essentially free of hydrocarbons. Clean water 181 and may be pumped to gaseous hydrocarbon saturator 215 where it may be mixed with the heated hydrocarbon feedstock 210. A small part of the water may be rejected as QW blowdown 235.

Figure 3:
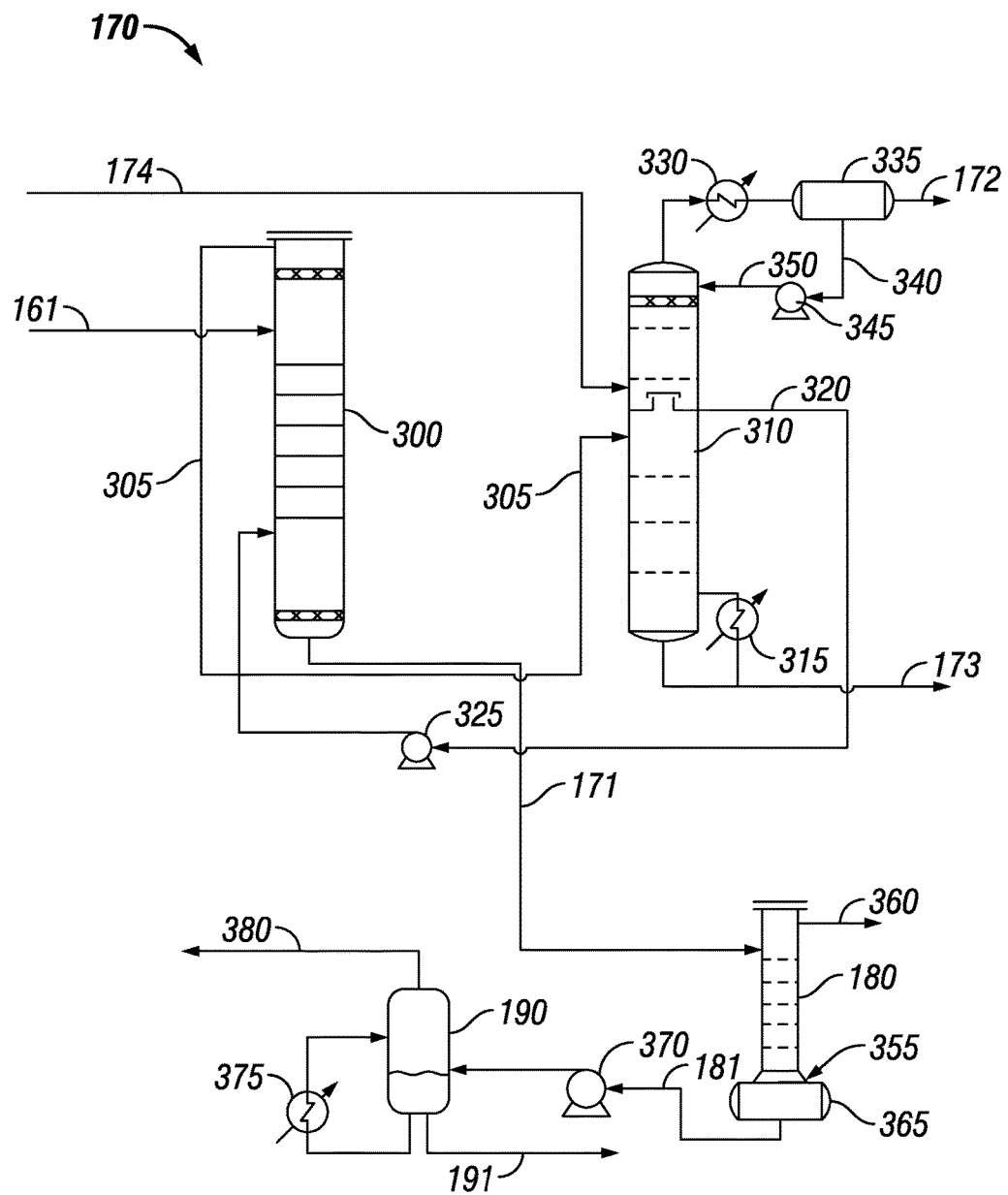
FIG. 3 is a schematic illustration of a dissolved oil removal unit.

With reference to FIG. 3, dissolved oil removal unit 170 and low pressure water stripper 180 from FIGS. 1 and 2 are shown in greater detail, in accordance with example embodiments. Coalesced NQW 161 from upstream oil coalescing unit, DOX or IGF, may comprise dissolved hydrocarbons and trace amount of emulsified oil particularly during upsets in the coalescing unit. Coalesced NQW 161 may be fed to a liquid-liquid extraction tower 300 where it may be countercurrently contacted with an extraction solvent, such as stabilized, hydrogenated, aromatic-rich gasoline, preferably a $C_6$-$C_8$ cut, with toluene, or a mixture thereof, fed to the top of the extraction tower. Contacting coalesced NQW 161 with the extraction solvent may remove from the quench water the polymer precursors such as styrene, indenes and dienes. Removing the precursors that may polymerize when exposed to high temperatures in the downstream water stripper and the dilution steam generator may reduce the fouling in the equipment.

The liquid-liquid extraction tower 300 may operate counter currently to contact the net quench water and extraction solvent to reduce emulsion formation. Liquid-liquid extraction tower 300 may operate at a pressure ranging from about 2 to about 10 bar gauge and a temperature ranging from about 50° C. to about 100° C. Liquid-liquid extraction tower 300 may be a multistage mixer-settler type tower, a plate/tray type tower, or a packed tower. The liquid-liquid extraction step may effectively transfer the polymerizable styrene, indenes, dienes, carbonyls, and heavy organic molecules from the aqueous phase to the extracting solvent phase. By the extraction step, greater than about 90% of the polymerizable materials may be removed. In some examples, greater than about 99% of the polymeric materials and polymer forming styrene, indenes, dienes and aromatic vinyl compounds may be removed. The spent extracting solvent 305 may pass out of the upper part of liquid-liquid extraction tower 300, and may then be passed to the middle part of extracting solvent regenerator unit 310 for recovery. The resulting, extracted quench water 171 may be removed from the bottom of the extraction tower and may be fed to the top of the low pressure water stripping unit 180.

Spent extracting solvent 305 and makeup solvent stream 174 may be distilled and regenerated in extracting solvent regenerator 310 that may comprise a fractionation column equipped with reboiler 315. Reboiler 315 may be heated with desuperheated medium pressure steam, and may be a thermosiphon reboiler. Extracting solvent regenerator 310 may operate at any suitable conditions, including, but not limited to, a pressure ranging from about 400 mm Hg to about 1 bar gauge and a temperature ranging from about 100° C. to about 160° C. Regenerated extracting solvent 320 may be removed from the middle chimney tray in solvent regenerator 310 and may be recycled back via pump 325 to the bottom of liquid-liquid extraction tower 300. The overhead of the regenerator 310 comprising the light hydrocarbon precursors may be condensed in condenser 330 and sent to the reflux drum 335. A portion of the liquid from reflux drum 335 is the reflux liquid 340, which may be pumped via pump 345 and the pumped reflux liquid 350 may be fed back to regenerator 310. Purge stream 172 from reflux drum 335 may be either returned to the quench water tower or purged to flare. The bottoms 173 comprising heavy hydrocarbons including polymers and polymer precursors may be removed for routing to the tar drum (not shown) for disposal.

The net quench water in contact with the extracting solvent in liquid-liquid extraction tower 300 may become saturated with the aromatic components of the extracting solvent. These may be stripped out in low pressure water stripper 180. The steam stripping of the extracted quench water may result in the removal of essentially 99.9% of the benzene and light materials and potentially more than 99% of the toluene by mass. In some embodiments, low pressure water stripper 180 may be a 10 to 20 tray column that utilizes low-pressure steam 355 added as the vapor phase for stripping.

Low pressure water stripper 180 may be operated at any suitable temperature, including, but not limited to, a saturation temperature ranging from about 125° C. to about 145° C. to provide improved volatile organic content (VOC) removal. Higher temperatures may be employed in low pressure water stripper 180, without fouling, to affect improved benzene and toluene removal, because of the removal of the polymer precursors in the upstream liquid-liquid extraction tower 300. In some embodiments, pressure from about 2 bar gauge to about 3 bar gauge may be maintained in low pressure water stripper 180 to recycle the overhead vapor stream 360 comprising steam and hydrocarbons to the quench water tower. The stripped bottoms 181 removed from stripper bottom drum 365 is the treated quench water (pretreated quench water); the treated quench water 181 may be pumped via pump 370 into dilution steam generator 190. The treated quench water from dilution steam generator 190 may be heated to generate steam in boiler 375. The steam is returned to dilution steam generator 190, where condensates and any contaminants may fall to the vessel bottom. Dilution steam 380 may be withdrawn from the top. Blowdown 191 may be removed from the bottom. Because of the relative purity of the NQW feed to the dilution steam generator (DSG), the blowdown may be substantially reduced, and instead of a trayed column and boiler, only a drum and a boiler may be required to produce dilution steam in accordance with embodiments of the present invention. Also the blowdown as disclosed herein may contain <10 ppbw benzene thus it may be safely discharged to the environment, where allowed, or used as water wash in the cracked gas compressor, or be added as makeup to the cooling towers.

Figure 4:
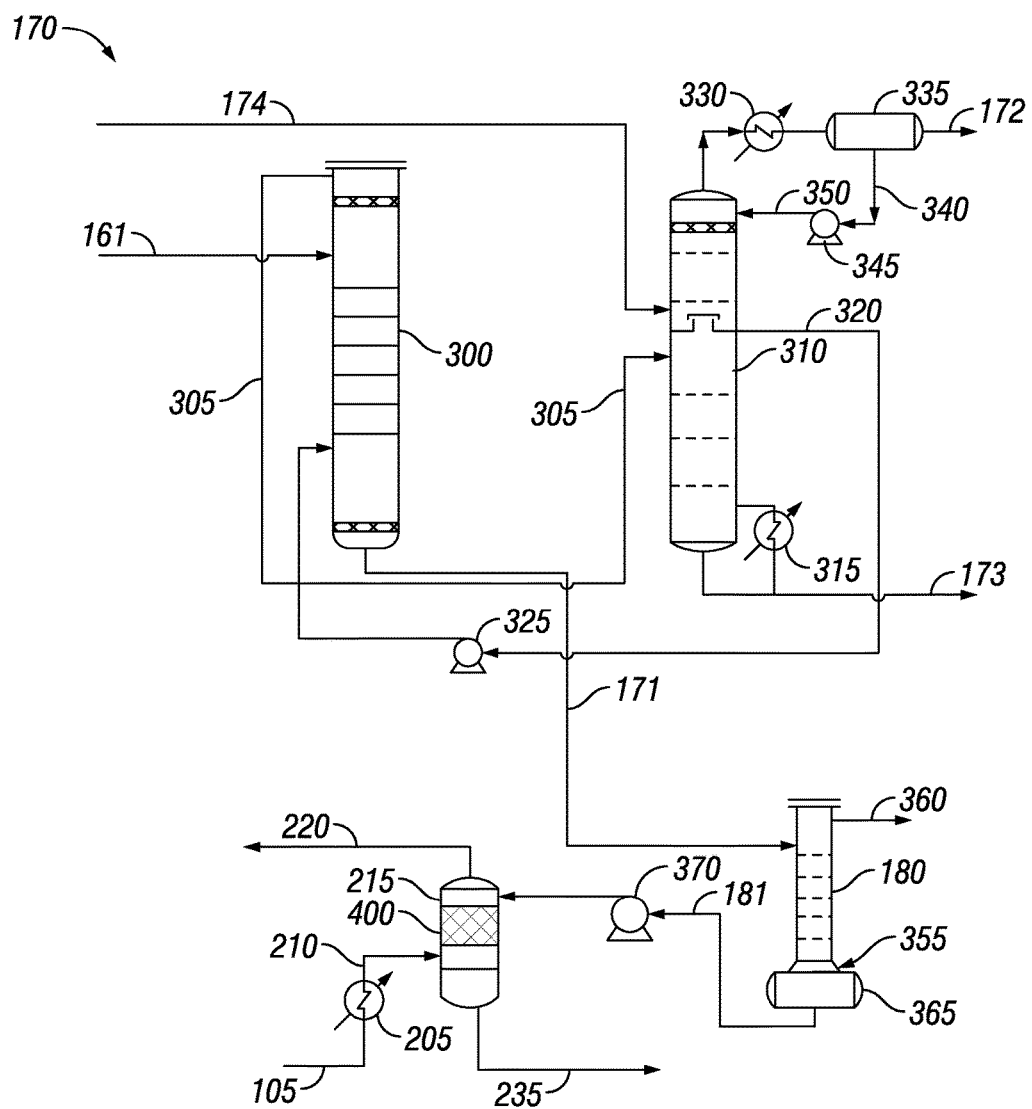
FIG. 4 is a schematic illustration of a dissolved oil removal unit.

With reference now to FIG. 4 which is the same as in FIG. 3 except that the pumped treated quench water from the low pressure water stripper 180 flows to the top of gaseous hydrocarbon saturator 215. Gaseous hydrocarbon saturator 215 may comprise a packed section 400. Gaseous hydrocarbon feedstock 105 may be heated in heat exchanger 205 to produce heated hydrocarbon gas 210 which may subsequently enter the bottom of the gaseous hydrocarbon saturator 215 which may flow up the saturator and counter currently contact the flowing treated clean water 181 through packed section 400. The hot hydrocarbon gas evaporates and carries the water vapor as dilution steam to produce mixed hydrocarbon and steam stream 220. Mixed hydrocarbon and steam stream 220 may flow to cracking furnaces 110. Blowdown 235 may be removed from the bottom of the gaseous hydrocarbon saturator 215. Because of the relative purity of clean water 181 feed to the saturator, the blowdown may contain <10 ppb benzene thus it may be safely discharged to the environment, where allowed, or used as water wash in the cracked gas compressor, or be added as makeup to the cooling towers.

The present disclosure may further comprise one or more of the following embodiments in any combination.

A system comprising a definitive sequence of unit operations to provide an overall treatment method of water conditioning to remove essentially all oils and particulate matter from water to allow for the production of high quality dilution steam for thermal cracking of gaseous feedstocks towards the production of lower olefins whereby the sequence of unit operations specifically comprises: a) oily-water separations of tars from heavy aromatics and water by decantation within three separate compartments whereby the first of three compartments separates tars whose specific gravity is greater than unity from water and the second of three compartments separates water from heavy aromatics/gasoline whose specific gravity is less than unity and the third of three compartments separates heavy aromatics/gasoline from water, followed by, b) either dispersed oil extractor (DOX) and/or induced gas flotation (IGF), followed by, c) filtration of fine particulate matter from the bulk aqueous phase, followed by, d) dissolved oil removal by liquid/liquid (L/L) extraction using a highly mono-aromatic solvent with capabilities to regenerate the spent solvent re-use to the L/L Extractor, followed by, e) in-situ coalescence of water from oil and oil from water preferably both from the head and heal of the L/L Extractor respectively or less preferably as external coalescer(s) in the same position relative to the extract and raffinate exit streams of the L/L Extractor, followed by, f) low pressure direct or indirect steam stripping to removal volatile organics from the aqueous phase whereby these organics have a lower vapor pressure than water at said low pressure conditions, followed by, g) either high pressure indirect steam stripping to vaporize the aqueous phase whereby the residual organics have a higher vapor pressure than water at said high pressure conditions, or, the application of a feed saturator to vaporize the aqueous phase with feed gas prior to entry to the cracking furnace, and, wherein high quality water is used for dilution steam as diluent for the (gas) cracker plant.

The method described by part a above, wherein the oil-water separations operate at a pressure relative to a temperature approach to adiabatic saturation whereby the operating temperature is typically ranges from a minimum of 80° C. to a maximum of 90° C. whereby decantation occurs at a steady state temperature profile using the principles of Stoke's Law for the three-phase separation of tars, heavy oils/gasoline and water; however, decantation can more preferably take place with two, two-phase whereby the first of two decantations separates tars from water and the second of two decantaions separates heavy oils/gasoline from water.

The method described by part b above, wherein the dispersed oil extractor (DOX) uses course filtration using specific coalescers, one primary and one secondary whereby the primary initiates coalescence and removes solids and tars while the secondary serves as an enhancer with a resultant typical removal of "oil and grease" (O&G) from about 1044 wppm to about 12.3 wppm with lesser removal of dissolved oils as "total organic carbon" (TOC) to levels from about 1614 wppm to about 350 wppm and finally "total suspended solids" (TSS) from about 22 wppm to about 3 wppm; however, the application of induced gas flotation (IGF) can be equally applied with similar results but most preferably applied in series with dispersed oil extractor.

The method described by part b and c above, wherein the dispersed oil extractor (DOX) uses course filtration using specific coalescers, one primary and one secondary whereby the primary initiates coalescence and removes solids and tars while the secondary serves as an enhancer with a resultant typical removal of "oil and grease" (O&G) from about 1044 wppm to about 12.3 wppm with lesser removal of dissolved oils as "total organic carbon" (TOC) to levels from about 1614 wppm to about 350 wppm and finally "total suspended solids" (TSS) from about 22 wppm to about 3 wppm; however, the application of induced gas flotation (IGF) can he equally applied with similar results but most preferably applied in series with dispersed oil extractor and wherein the aqueous phase is received from either DOX or IGF at a temperature range at minimum of 80° C. or maximum of 90° C. at a pressure compatible with the overall pressure profile for the purpose of fine filtration for micron size particles of 5 μm or more to allow higher reliability of coalescence within the next unit operation.

The method described by part d above, wherein a frayed or most preferably a packed multi-stage countercurrent L/L Extractor with either random or structured packing contacting the aqueous phase having contained dissolved oils with a highly mono-aromatic solvent preferably benzene of a mixed benzene, toluene with mix xylenes or most preferably merchantable grade toluene at a temperature range of about 60° C. 80° C., preferably at 70° C. or most preferably at 80° C. whereby the S/F ratio is most preferably 1:8 and no less operating at elevated pressure but no higher pressure than available to satisfy the overall pressure profile wherein said spent solvent is regenerated by atmospheric distillation (e.g. 760 mm Hg) or more preferably by slight vacuum (no less than 600 mm Hg) to mitigate the fouling tendencies of the residual oils concentrated at the bottoms outlet such that the reboiler operates as a once-thru reboiler with no more than 15% vaporization but more preferably less than 15% vaporization.

The method described by part e above, further comprising receiving the aqueous phase from fine filtration to allow coalescence by a discrete coalescer to remove free oils to the extent of their mutual solubility in water with no removal of dissolved oils whereby in-situ coalescence at head and heal of the L/L Extractor removes water from oil (solvent) and oil (solvent) from water respectively, while the same can be accomplished less preferably using external coalescer(s).

The method described by part e above, whereby concentrations of dissolved oils mimicked experimentally by way of contained styrene and indene is less than 1 wppm total within the final sequence of treatment; more specifically, the water quality for styrene content of no more than 0.3 wppm from 55 wppm and water quality for indene content of no more than 0.4 wppm from 410 wppm using a solvent-to-feed (S/F) ratio of no less than 1:8 using either toluene or BTX within a L/L Extractor per the sequence of unit operations as previously described.

The method described by part f above, further comprising wherein the extract from the L/L Extractor now comprises a styrene content of no more than 0.3 wppm from 55 wppm and water quality for indene content of no more than 0.4 wppm from 410 wppm, such that all remaining hydrocarbons which have a higher vapor pressure than water can be readily stripped at low pressure wherein atmospheric or slightly higher than atmospheric is highly desirable to ensure no light key hydrocarbons are contained in the aqueous phase for final dilution steam quality.

The method described by part g above, further comprising wherein the extract from the L/L Extractor is now comprises a styrene content of no more than 0.3 wppm from 55 wppm and water quality for indene content of no more than 0.4 wppm from 410 wppm such that all remaining hydrocarbons which have a lower vapor pressure than water can be readily stripped at high pressure compatible wherein the pressure profile for the final unit operation is highly desirable to ensure no heavy key hydrocarbons are contained in the aqueous phase for final dilution steam quality.

The method for the final unit operation in the sequence described herein provides a reject aqueous stream exiting the bottom of the high pressure stripper, when applied, or a reject aqueous stream exiting the bottom of the feed saturator, when applied, whereby the quality of reject water is suitable for total recovery and return to the first unit operation (oily-water separation) thereby allowing for no loss of water from the system resulting in no make-up water to the system. To permit steady-state operation of the oily-water separation within the first unit operation, cooling of the reject water from either high pressure stripping or feed saturation is required to ensure temperature profile compatibility between unit operations, i.e. oily-water separation and dilution steam production.

EXAMPLES

To facilitate a better understanding of the present embodiments, the following illustrative examples of some of the embodiments are given. In no way should such examples be read to limit, or to define, the scope of the disclosure.

The removal of styrene and indene from the quench water (QW) stream in the example embodiments may be further illustrated by the following examples wherein all percentages are by weight unless specified otherwise. A gas chromatography (GC) method was used to evaluate the composition of styrene and indene in the quench water stream. Liquid samples were collected by filling sample bottles from the extractor column overhead outlet. Each sample was then analyzed by GC to determine the amount of styrene and indene in the quench water.

The Extraction Column consisted of 5 cm inside diameter stainless steel column, packed with 6 mm Propak® stainless steel packing to a height of 90 cm. Quench water that contained 55 ppmw (parts per million by weight) styrene and 410 ppmw indene was allowed to flow down the column packing contacting counter currently against the up flowing hydrocarbon solvent (toluene or BTX). The extraction column was operated at 0.9 barg (bar gauge) and temperature of 40° C. The solvent flow rate to the bottom of the extraction column was adjusted to flow at a predetermined rate for each test run; while the liquid quench water flow to the top of the column was set to flow at a rate of 12±1 liter/hr. for all test runs; the flow rates to the column were calculated for operation well below the flooding regime of the packing.

The treated quench water from the extractor flowed directly to the top of the quench water stripper operated at 0.2 barg. The stripper consisted of 5 cm inside diameter stainless steel column, packed with 6 mm Propak® stainless steel packing to a height of 90 cm. The quench water was reboiled at the bottom of the stripper; the generated steam flowed up the column stripping the more volatile residual styrene and indene from the liquid quench water flowing down the column through the packed section. The styrene and indene were stripped to <<0.3 ppmw.

The solvent from the extractor was collected in a drum and then pumped to the middle of the of the regenerator column with a runback, vented, condenser operated at 0.3 barg. The regenerator consisted of 5 cm inside diameter stainless steel column, packed with 6 mm Propak® stainless steel packing with a feed section placed in the middle of the column with a packed height of 60 cm above the feed section and a packed height of 60 cm below the feed section. The solvent was distilled and the dissolved light gases that were picked up by the solvent from the QW during extraction were vented from the condenser vent. The heavy styrene and indene was purged with some of the solvent from the bottom of the regenerator column. The purified solvent was taken out of the column and kept in a storage drum for use in the next test run.

Example 1

The extraction column was operated with quench water flow of 12±1 liter/hr. containing 55 ppmw styrene and 410 ppmw indene which was fed to the top of the column, and contacted counter-currently with toluene solvent fed to the bottom of the packing at a rate of 12±1 liter/hr. The Toluene to quench water volumetric ratio is 1:1. The styrene and indene from the quench water is extracted by the toluene, and their concentration in the quench water is depleted at the column bottom outlet stream, measured an average 0.41 ppmw styrene, and an average of 0.45 ppmw indene. The quench water from the extractor was fed directly to the top of quench water stripper where it was stripped by steam generated in the bottom reboiler. The concentrations of styrene and indene were further reduced in the quench water stream leaving the bottom of the stripper to an average 0.12 ppmw styrene, and an average of 0.16 ppmw indene. Data for Example 1 is shown in Table 1.

TABLE 1

| LLE inlet QW | styrene | 55 | ppmw |
| --- | --- | --- | --- |
|  | indene | 410 | ppmw |
| QW flow rate |  | 12 ± 1 | liter/hr. |
| Toluene flow rate |  | 12 ± 1 | liter/hr. |
| Toluene/QW | vol Ratio | 1:1 |  |
| Extractor | ID | 5 | cm |
| Packed Height |  | 90 | cm |
| packing type | Propak ® | 6 | mm |

| | Run time minutes | Run # | LLE outlet QW styrene ppmw | LLE outlet QW indene ppmw | LPWS outlet QW styrene ppmw | LPWS outlet QW indene ppmw |
| --- | --- | --- | --- | --- | --- | --- |
| | 88 | 1 | 0.7 | 0.6 | 0.2 | 0.4 |
| | 82 | 2 | 0.3 | 0.5 | 0.1 | 0.1 |
| | 75 | 3 | 0.33 | 0.45 | 0.1 | 0.1 |
| | 88 | 4 | 0.3 | 0.3 | 0.1 | 0.1 |
| | 80 | 5 | 0.4 | 0.38 | 0.1 | 0.1 |
| Avg | 83 | | 0.41 | 0.45 | 0.12 | 0.16 |

Example 2

The extraction column was operated with quench water flow of 12±1 liter/hr. containing 55 ppmw styrene and 410 ppmw indene which was fed to the top of the column, and contacted counter-currently with toluene solvent fed to the bottom of the packing at a rate of 2.5±0.2 liter/hr. The toluene to quench water volumetric ratio was 1:4.8 The styrene and indene from the quench water was extracted by the toluene, and their concentration in the quench water was depleted at the column bottom outlet stream, measured an average 0.91 ppmw styrene, and an average of 0.74 ppmw indene. The quench water from the extractor was fed directly to the top of quench water stripper where it was stripped by steam generated in the bottom reboiler. The concentrations of styrene and indene were further reduced in the quench water stream leaving the bottom of the stripper to an average 0.2 ppmw styrene, and an average of 0.2 ppmw indene. Data for Example 2 is shown in Table 2.

TABLE 2

| | | LLE inlet QW | | |
|---|---|---|---|---|
| LLE inlet QW | styrene | | 55 | ppmw |
| | indene | | 410 | ppmw |
| QW flow rate | | | 12 ± 1 | liter/hr. |
| Toluene flow rate | | | 2.5 ± 0.2 | liter/hr. |
| Toluene/QW | vol Ratio | | 1:4.8 | |
| Extractor | ID | | 5 | cm |
| Packed Height | | | 90 | cm |
| packing type | Propak ® | | 6 | mm |

| | | LLE outlet QW | | LPWS outlet QW | |
|---|---|---|---|---|---|
| Run time minutes | Run # | styrene ppmw | indene ppmw | styrene ppmw | indene ppmw |
| 81 | 1 | 1.2 | 0.8 | 0.2 | 0.4 |
| 90 | 2 | 1 | 0.9 | 0.3 | 0.1 |
| 75 | 3 | 0.53 | 0.6 | 0.2 | 0.1 |
| 80 | 4 | 0.9 | 0.65 | 0.1 | 0.2 |
| Avg 82 | | 0.91 | 0.74 | 0.20 | 0.20 |

Example 3

The extraction column was operated with quench water flow of 12±1 liter/hr. containing 55 ppmw styrene and 410 ppmw indene which was fed to the top of the column, and contacted counter-currently with toluene solvent fed to the bottom of the packing at a rate of 1.5±0.1 liter/hr. The Toluene to quench water volumetric ratio was 1:8. The styrene and indene from the quench water was extracted by the toluene, and their concentration in the quench water is depleted at the column bottom outlet stream, measured an average 1.13 ppmw styrene, and an average of 0.9 ppmw indene. The quench water from the extractor was fed directly to the top of quench water stripper where it is stripped by steam generated in the bottom reboiler. The concentrations of styrene and indene were further reduced in the quench water stream leaving the bottom of the stripper to an average 0.23 ppmw styrene, and an average of 0.3 ppmw indene. Data for Example 3 is shown in Table 3.

Example 4

The extraction column was operated with quench water flow of 12±1 liter/hr. containing 55 ppmw styrene and 410 ppmw indene which was fed to the top of the column, and contacted counter-currently with BTX solvent fed to the bottom of the packing at a rate of 2.5±0.2 liter/hr. The BTX to quench water volumetric ratio was 1:4.8. The styrene and indene from the quench water was extracted by the BTX, and their concentration in the quench water was depleted at the column bottom outlet stream, measured an average 0.75 ppmw styrene, and an average of 1.8 ppmw indene. The quench water from the extractor was fed directly to the top of quench water stripper where it is stripped by steam generated in the bottom reboiler. The concentrations of styrene and indene were further reduced in the quench water stream leaving the bottom of the stripper to an average 0.28 ppmw styrene, and an average of 0.25 ppmw indene. Data for Example 4 is shown in Table 4.

TABLE 3

RUNS TEST 3
QUENCH WATER TREATIN
DISSOLVED OIL REMOVAL UNIT (DOR)

| | | | | |
|---|---|---|---|---|
| LLE inlet QW | styrene | | 55 | ppmw |
| | indene | | 410 | ppmw |
| QW flow rate | | | 12 ± 1 | liter/hr. |
| Toluene flow rate | | | 1.5 ± 0.1 | liter/hr. |
| Toluene/QW | vol Ratio | | 1:8 | |
| Extractor | ID | | 5 | cm |
| Packed Height | | | 90 | cm |
| packing type | Propak ® | | 6 | mm |

| | | LLE outlet QW | | LPWS outlet QW | |
|---|---|---|---|---|---|
| Run time minutes | Run # | Styrene ppmw | indene ppmw | styrene ppmw | indene ppmw |
| 72 | 1 | 1.5 | 1 | 0.2 | 0.4 |
| 75 | 2 | 1.2 | 0.9 | 0.3 | 0.3 |
| 82 | 3 | 0.7 | 0.7 | 0.2 | 0.3 |
| 80 | 4 | 1.1 | 1 | 0.2 | 0.2 |
| Avg 77 | | 1.13 | 0.90 | 0.23 | 0.30 |

TABLE 4

**RUNS TEST 4
QUENCH WATER TREATING
DISSOLVED OIL REMOVAL UNIT (DOR)**

| LLE inlet QW | styrene | 55 | ppmw |
| --- | --- | --- | --- |
|  | indene | 410 | ppmw |
| QW flow rate |  | 12 ± 1 | liter/hr. |
| BTX flow rate |  | 2.5 ± 0.2 | liter/hr. |
| BTX/QW | vol Ratio | 1:4.8 |  |
| Extractor | ID | 5 | cm |
| Packed Height |  | 90 | cm |
| packing type | Propak ® | 6 | mm |

|  | Run time minutes | Run # | LLE outlet QW | | LPWS outlet QW | |
| --- | --- | --- | --- | --- | --- | --- |
|  |  |  | Styrene ppmw | indene ppmw | styrene ppmw | indene ppmw |
|  | 85 | 1 | 0.8 | 2.1 | 0.3 | 0.4 |
|  | 78 | 2 | 1 | 1.9 | 0.3 | 0.2 |
|  | 75 | 3 | 0.7 | 1.6 | 0.2 | 0.2 |
|  | 85 | 4 | 0.5 | 1.6 | 0.3 | 0.2 |
| Avg | 77 |  | 0.75 | 1.8 | 0.28 | 0.25 |

Example 5

The extraction column was operated with quench water flow of 12±1 liter/hr. containing 55 ppmw styrene and 410 ppmw indene which was fed to the top of the column, and contacted counter-currently with BTX solvent fed to the bottom of the packing at a rate of 1.5±0.1 liter/hr. The BTX to quench water volumetric ratio was 1:8. The styrene and indene from the quench water is extracted by the BTX, and their concentration in the quench water was depleted at the column bottom outlet stream, measured an average 1.43 ppmw styrene, and an average of 2.23 ppmw indene. The quench water from the extractor was fed directly to the top of quench water stripper where it is stripped by steam generated in the bottom reboiler. The concentrations of styrene and indene were further reduced in the quench water stream leaving the bottom of the stripper to an average 0.28 ppmw styrene, and an average of 0.35 ppmw indene. Data for Example 5 is shown in Table 5.

SUMMARY OF RESULTS

Results of the Examples 1, 2, 3, 4 and 5 show that removal of styrene and indene are almost complete when the quench water from the DOX/IGF units is extracted by light aromatic hydrocarbon solvents e.g. toluene and BTX. DOR removes >99% of the incoming polymer precursors (styrene and indene) in the quench water from the DOX/IGF units. The Solvent could be either toluene or BTX. DOR will prevent fouling in the LPWS and the dilution steam generating equipment both the DSG and the Saturators. The results are summarized in Table 6.

TABLE 5

**RUNS TEST 5
QUENCH WATER TREATING
DISSOLVED OIL REMOVAL UNIT (DOR)**

| LLE inlet QW | styrene | 55 | ppmw |
| --- | --- | --- | --- |
|  | indene | 410 | ppmw |
| QW flow rate |  | 12 ± 1 | liter/hr. |
| BTX flow rate |  | 1.5 ± 0.1 | liter/hr. |
| BTX/QW | vol Ratio | 1:8 |  |
| Extractor | ID | 5 | cm |
| Packed Height |  | 90 | cm |
| packing type | Propak ® | 6 | mm |

|  | Run time minutes | Run # | LLE outlet QW | | LPWS outlet QW | |
| --- | --- | --- | --- | --- | --- | --- |
|  |  |  | Styrene ppmw | indene ppmw | styrene ppmw | indene ppmw |
|  | 70 | 1 | 1.5 | 2.5 | 0.3 | 0.4 |
|  | 75 | 2 | 1.4 | 2 | 0.3 | 0.3 |
|  | 88 | 3 | 1.7 | 1.9 | 0.2 | 0.3 |
|  | 78 | 4 | 1.1 | 2.5 | 0.3 | 0.4 |
| Avg | 78 |  | 1.43 | 2.23 | 0.28 | 0.35 |

TABLE 6

| RUNS | | | Inlet QW from DOX/IGF | | DOR-LLE Extractor Outlet | | DOR-LPWS Outlet | |
|---|---|---|---|---|---|---|---|---|
| TEST # | Extraction Solvent | Solvent/QW Vol Ratio | Styrene ppmw | Indene ppmw | Styrene ppmw | Indene ppmw | Styrene ppmw | Indene ppmw |
| 1 | Toluene | 1:1 | 55 | 410 | 0.41 | 0.45 | 0.12 | 0.16 |
| 2 | Toluene | 1:4.8 | 55 | 410 | 0.91 | 0.74 | 0.20 | 0.20 |
| 3 | Toluene | 1:8 | 55 | 410 | 1.13 | 0.90 | 0.23 | 0.30 |
| 4 | BTX | 1:4.8 | 55 | 410 | 0.75 | 1.8 | 0.28 | 0.25 |
| 5 | BTX | 1:8 | 55 | 410 | 1.43 | 2.23 | 0.28 | 0.35 |

What is claimed is:

1. A method for removing dissolved hydrocarbons from water comprising:

mixing a gaseous hydrocarbon stream with a clean steam stream to produce a mixed hydrocarbon stream;

cracking the mixed hydrocarbon stream in a cracking furnace to produce a cracked gas effluent;

quenching the cracked gas effluent in a quench water tower with quench water to produce a quenched gas stream and a spent quench water stream comprising water, tars, heavy aromatic hydrocarbons, gasoline, dissolved oil, and dispersed oil;

decanting the spent quench water stream to remove at least a portion of the tars, the heavy aromatic hydrocarbons, and the gasoline from the spent quench water stream to produce a decanted spent quench water stream;

feeding the decanted spent quench water stream to a dispersed oil removal unit wherein the dispersed oil removal unit removes at least a portion of the dispersed oil from the decanted spent quench water to produce a coalesced quench water stream and wherein the dispersed oil removal unit is selected from the group consisting of a filter coalescer unit, dispersed oil extractor unit, induced gas floatation unit, and combinations thereof;

feeding the coalesced quench water stream to a liquid-liquid extraction unit wherein the liquid-liquid extraction unit removes at least a portion of the dissolved oil and produce an extracted effluent stream;

feeding the extracted effluent stream to a low pressure water stripper wherein the effluent stream is stripped using a stripping steam stream to produce a cleaned water effluent; and vaporizing the cleaned water effluent in a dilution steam generator to produce the clean steam stream.

2. The method of claim 1 wherein the step of decanting operates at a temperature of about 80° C. to about 90° C. and a pressure within about 90-100% of adiabatic saturation.

3. The method of claim 1 wherein the dispersed oil removal unit comprises the filter coalescer unit, and wherein the filter coalescer unit comprises a primary coalescer and secondary coalescer and wherein the filter coalescer reduces a total organic carbon level to less than about 350 ppmw.

4. The method of claim 1 wherein the liquid-liquid extraction unit comprises a liquid-liquid extraction column and a solvent regenerator.

5. The method of claim 4 wherein the liquid-liquid extraction column receives the coalesced quench water stream and counter currently contacts the coalesced quench water steam with an aromatic solvent.

6. The method of claim 5 wherein the aromatic solvent is a mono-aromatic solvent selected from the group consisting of mono-aromatic $C_6$-$C_8$ cut gasoline, toluene, benzene, xylene, and combinations thereof.

7. The method of claim 1 wherein the extracted effluent stream comprises less than 1.5 ppmw styrene and less than 3 ppmw indene.

8. The method of claim 1 wherein a steam blowdown stream from the dilution steam generator contains less than 10 ppmw total organic carbon.

9. A method for removing dissolved hydrocarbons from water comprising:

heating a gaseous hydrocarbon stream to produce a heated hydrocarbon stream and feeding the heated hydrocarbon stream to a hydrocarbon saturator;

introducing a cleaned water effluent into the hydrocarbon saturator wherein the heated hydrocarbon stream and cleaned water effluent mix and vaporize at least a portion of the water and produce a mixed hydrocarbon stream;

cracking the mixed hydrocarbon stream in a cracking furnace to produce a cracked gas effluent;

quenching the cracked gas effluent in a quench water tower with quench water to produce a quenched gas stream and a spent quench water stream comprising water, tars, heavy aromatic hydrocarbons, gasoline, dissolved oil, and dispersed oil;

decanting the spent quench water stream to remove at least a portion of tars, heavy aromatic hydrocarbons, and gasoline from the spent quench water stream to produce a decanted spent quench water stream;

feeding the spent quench water stream to a dispersed oil removal unit wherein the dispersed oil removal unit removes at least a portion of the dispersed oil from the decanted spent quench water to produce a coalesced quench water stream and wherein the dispersed oil removal unit is selected from the group consisting of filter coalescer unit, dispersed oil extractor unit, induced gas floatation unit, and combinations thereof;

feeding the coalesced quench water stream to a liquid-liquid extraction unit wherein the liquid-liquid extraction unit removes at least a portion of the dissolved oil and produces an effluent stream comprising less than 4 ppmw total dissolved oil; and feeding the effluent stream to a low pressure water stripper wherein the effluent stream is stripped using a stripping steam stream to produce the cleaned water effluent.

10. The method of claim 9 wherein the step of decanting operates at a temperature of about 80° C. to about 90° C. and a pressure within about 90-100% of adiabatic saturation.

11. The method of claim 9 wherein the dispersed oil removal unit comprises the filter coalescer unit, and wherein the filter coalescer unit comprises a primary coalescer and secondary coalescer and wherein the filter coalescer reduces a total organic carbon level to less than about 350 ppmw.

12. The method of claim 9 wherein the liquid-liquid extraction unit comprises a liquid-liquid extraction column and a solvent regenerator.

13. The method of claim 12 wherein the liquid-liquid extraction column receives the coalesced quench water stream and counter currently contacts the coalesced quench water stream with an aromatic solvent.

14. The method of claim 13 wherein the aromatic solvent is a mono-aromatic solvent selected from the group consisting of mono-aromatic $C_6$-$C_8$ cut gasoline, toluene, benzene, xylene, and combinations thereof.

15. The method of claim 9 wherein the extracted effluent stream comprises less than 1.5 ppmw styrene and less than 2.3 ppmw indene, and less than 4 ppmw total dissolved oil.

16. The method of claim 9 wherein a steam blowdown stream from the dilution steam generator contains less than 10 ppmw total organic carbon.

17. A system for removing dissolved hydrocarbons from water comprising:
   a gas cracking furnace configured to crack a gaseous hydrocarbon stream;
   a quench water tower configured to quench an effluent stream from the gas cracking furnace;
   a decanter configured to decant a spent quench water stream from the quench water tower, the spent quench water stream comprising hydrocarbons;
   a dispersed oil removal unit configured to remove at least a portion of a dispersed oil from a decanter effluent stream, the dispersed oil removal unit being selected from the group consisting of a filter coalescer unit, a dispersed oil extractor unit, an induced gas floatation unit, and combinations thereof;
   a liquid-liquid extractor unit configured to remove at least a portion of a dissolved oil from a dispersed oil removal unit effluent stream; and
   a low pressure water stripper configured to contact a liquid-liquid extractor effluent stream with a stripping steam to produce a stream of cleaned water effluent, the clean water effluent containing less than about 1.0 ppmw hydrocarbons.

18. The system of claim 17 wherein the liquid-liquid extractor unit comprises a liquid-liquid extraction column and a solvent regenerator.

19. The method of claim 18 wherein the liquid-liquid extraction column is configured to receive the dispersed oil removal unit effluent stream and counter currently contact the dispersed oil removal unit effluent stream with an aromatic solvent.

20. The system of claim 17 further comprising a dilution steam generator configured to generate stream from the cleaned water effluent.

* * * * *